US005594115A

United States Patent [19]

Sharma

[11] Patent Number: 5,594,115
[45] Date of Patent: Jan. 14, 1997

[54] PROCESS OF PURIFYING RECOMBINANT PROTEINS AND COMPOUNDS USEFUL IN SUCH PROCESS

[75] Inventor: Satish K. Sharma, Portage, Mich.

[73] Assignee: Pharmacia & Upjohn Company, Kalamazoo, Mich.

[21] Appl. No.: 365,994

[22] Filed: Dec. 29, 1994

Related U.S. Application Data

[63] Continuation of Ser. No. 941,043, filed as PCT/US91/01543, Mar. 11, 1991, abandoned, which is a continuation-in-part of Ser. No. 506,605, Apr. 9, 1990, abandoned.

[51] Int. Cl.$^6$ .................... G01N 33/553; C12P 21/04
[52] U.S. Cl. .................... 530/413; 530/350; 435/69.7; 435/172.3; 436/525; 536/23.1; 536/23.4; 536/23.5
[58] Field of Search ............................ 530/350, 413; 436/525, 808; 435/172.3, 69.7; 536/23.4, 23.1, 23.5

[56] References Cited

U.S. PATENT DOCUMENTS

| 4,569,794 | 2/1986 | Smith | 260/113 |
|---|---|---|---|
| 4,751,180 | 6/1988 | Cousens | 435/68 |
| 4,782,137 | 11/1988 | Hopp | 530/328 |
| 5,202,259 | 4/1993 | Goff et al. | 435/252.33 |

FOREIGN PATENT DOCUMENTS

| 12709/88 | 9/1988 | Australia | C07K 3/20 |
|---|---|---|---|
| 0163573A1 | 5/1985 | European Pat. Off. | C12N 15/00 |
| 0184355A3 | 6/1986 | European Pat. Off. | C07K 17/02 |
| WO88/10299 | 12/1988 | WIPO | C12N 15/00 |

OTHER PUBLICATIONS

Sharma et al. 1992. Methods: A Companion to Methods in Enzymology 4:57–67.
Hochuli et al. 1988 Bio/Technology 6:1321–1325.
Smith, M. C. et al., "Chelating Peptide–Immobilzed Metal Ion Affinity Chromatography", J. Biol. Chem. 263(15):7211–7215, 1988.
Hochuli, E., et al., "New Metal Chelate Adsorbent Selective for Proteins and Peptides Containing Neighbouring Histidine Residues", J. Chromat. 411:177–184, 1987.
Ljungquist, C., et al. "Immobilization and Affinity Purification of Recombinant Proteins Using Histidine Peptide Fusions", Eur. J. Biochem. 186:563–569, 1989.
Haffey, M. L. et al., "Site–Specific Cleavage of a Fusion Protein by Renin", DNA, 6(6):565–571, 1987.
Hopp, T. P. et al., "A Short Polypeptide Marker Sequence Useful for Recombinant Protein Identification and Purification", Bio/Technol. 6:1204–1210, Oct. 1988.
Kreil, G., "Processing of Precursors by Dipeptidylaminopeptidases: A Case of Molecular Ticketing", TIBS 15:23–26, Jan. 1990.
Dalbøge, H. et al., "A Novel Enzymatic Method for Production of Authentic hGH from an Escherichia Coli Produced hGH–Precursor", Bio/Technol 5:161–164, Feb. 1987.
Dalbøge, H. et al., "Cloning and Expression of an Interleukin–1β Precursor and Its Conversion to Interleukin–1β", FEBS 246(1,2):89–93, Mar. 1989.
Dalbøge, H., et al., "In vivo Processing of N–Terminal Methionine in E. Coli", FEBS 266(1,2):1–3, Jun. 1990.
McDonald, J. K., et al., J. Biol. Chem. 244(10):2693–2709, May 1969.

Primary Examiner—Stephen G. Walsh
Assistant Examiner—Elizabeth E. Kemmerer
Attorney, Agent, or Firm—James D. Darnley, Jr.; Mark DeLuca

[57] ABSTRACT

Recombinant fusion proteins which comprise a biologically active polypeptide portion and metal chelating peptide are disclosed. The fusion proteins contain metal chelating peptides which have at least three and preferably six alternating histidine residues. Fusion proteins which contain metal chelating peptides that are substrates for dipeptidylpeptidase I are also disclosed. Additionally, a method of obtaining desired polypeptides by producing recombinant fusion proteins and purifying them with immobilized metal ions is disclosed. A kit for purifying desired polypeptides is also disclosed.

15 Claims, No Drawings

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

```
Met  Glu  His  Glu  His  Glu  His  Glu  His  Glu
1                   5                        10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met  Glu  His  Asp  His  Asp  His  Asp  His  Asp
1                   5                        10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Met  Ile  His  Asp  His  Asp  His  Asp  His  Asp
1                   5                        10
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Pro  Ile  His  Asp  His  Asp  His  Pro  Phe  His  Leu  Val  Ile  His  Ser  Xaa
1                   5                             10                       15
```

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Pro  Ile  His  Asp  His  Asp  His  Pro  Phe  His  Leu  Leu  Tyr  Tyr  Ser  Xaa
1                   5                             10                       15
```

( 2 ) INFORMATION FOR SEQ ID NO:6:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( x i ) SEQUENCE DESCRIPTION: SEQ ID NO:6:

```
Pro  Ile  Pro  Phe  His  Leu  Val  Ile  His  Ser  Xaa
1                   5                        10
```

( 2 ) INFORMATION FOR SEQ ID NO:7:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Pro  Ile  Pro  Phe  His  Leu  Leu  Tyr  Tyr  Ser  Xaa
1                   5                        10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Pro  Ile  His  Asp  His  Asp  His  Pro  Phe  His  Leu  Xaa
1                   5                        10
```

( 2 ) INFORMATION FOR SEQ ID NO:9:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:9:

```
AATTCATGCC  CATTCACGAT  CACGATCACC  CCTTTCACTT  AGTAATTCAC  AGCCCCATTA        60
GCCCT                                                                          65
```

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:10:

```
ATTGAGACTG  TACCAGTAAA  ATTAAAGCCA  GGAATGGATG  GCCCAAAAGT  TAAACAATGG        60
```

( 2 ) INFORMATION FOR SEQ ID NO:11:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:11:

```
CTAATGGGGC  TGTGAATTAC  TAAGTGAAAG  GGGTGATCGT  GATCGTGAAT  GGGCATG          57
```

( 2 ) INFORMATION FOR SEQ ID NO:12:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:12:

```
CCATTGTTTA ACTTTTGGGC CATCCATTCC TGGCTTTAAT TTTACTGGTA CAGTCTCAAT      60

AGGG                                                                  64
```

( 2 ) INFORMATION FOR SEQ ID NO:13:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:13:

```
AATTCATGCC CATTCACGAT CACGATCACC CCTTTCACTT ACTATACTAC AGCCCATTA       60

GCCCT                                                                 65
```

( 2 ) INFORMATION FOR SEQ ID NO:14:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:14:

```
CTAATGGGGC TGTAGTATAG TAAGTGAAAG GGGTGATCGT GATCGTGAAT GGGCATG         57
```

( 2 ) INFORMATION FOR SEQ ID NO:15:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:15:

```
AATTCATGCC CATTCCCTTT CACTTAGTAA TTCACAGCCC CATTAGCCCT                 50
```

( 2 ) INFORMATION FOR SEQ ID NO:16:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:16:

```
CTAATGGGGC TGTGAATTAC TAAGTGAAAG GGAATGGGCA TG                         42
```

( 2 ) INFORMATION FOR SEQ ID NO:17:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:17:

```
AATTCATGCC  CATTCCCTTT  CACTTACTAT  ACTACAGCCC  CATTAGCCCT                    50
```

( 2 ) INFORMATION FOR SEQ ID NO:18:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:18:

```
CTAATGGGGC  TGTAGTATAG  TAAGTGAAAG  GGAATGGGCA  TG                            42
```

( 2 ) INFORMATION FOR SEQ ID NO:19:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:19:

```
AATTCATGCC  CATTCACGAT  CACGATCACC  CCTTTCACTT  A                             41
```

( 2 ) INFORMATION FOR SEQ ID NO:20:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:20:

```
GTACGGGTAA  GTGCTAGTGC  TAGTGGGGAA  AGTGAATGAT  C                             41
```

PROCESS OF PURIFYING RECOMBINANT PROTEINS AND COMPOUNDS USEFUL IN SUCH PROCESS

This application is a file wrapper continuation of U.S. Ser. No. 07/941,043, filed Oct. 2, 1992, now abandoned, which is the National Stage of International Application PCT/US91/01543, filed Mar. 11, 1991; which is a continuation-in-part application of U.S. Ser. No. 07/506,605, filed Apr. 9, 1990, now abandoned.

FIELD OF THE INVENTION

The present invention relates to a method of obtaining a purified desired protein product by producing it as a recombinant fusion protein in a host, purifying the fusion protein and cleaving it into constitutive proteins.

BACKGROUND OF THE INVENTION

The rapid developments in recombinant DNA methodology have allowed the production of polypeptides, proteins, and their analogs in unlimited quantities in a very short period of time. These developments have created a need to handle purification of these proteins from complex mixtures in highly efficient and predictable manners.

Recombinant DNA technology may be used for the production of desired polypeptides and proteins in host cells. Genes for desired proteins may be isolated from the genetic material of cells which contain the gene in nature or they may be chemically synthesized. The isolated or chemically synthesized gene may be inserted and expressed in host cell systems which produce protein products at high levels.

The desired protein products must then be isolated and recovered from the total amount of protein produced by the host cells. The purification of heterologous polypeptides produced by host cells can be very expensive and can cause denaturation of the protein product itself. An overview of protein purification techniques is provided in the Background Art section of U.S. Pat. No. 4,782,137 issued Nov. 1, 1988 to Hopp et al, which is incorporated herein by reference. Among the methods to purify proteins that are described in Hopp, the most commonly practiced are ion-exchange, hydrophobic chromatography, and gel filtration. The major disadvantage of these approaches are the lack of specificity of each technique. Thus, these techniques are unsuitable to achieve pure protein in high yields. Even small changes in amino acid composition may change the purification properties. A modified purification procedure needs to be developed and optimized for each new protein. In the case of rDNA derived proteins, structural and functional consequences of heterologous gene expression (H. Bialy, Bio/technology, 5:884, 1987) are additional factors that may make it impossible to predict selection of these purification methods for a given protein.

Desired protein molecules may be isolated from complex mixtures by methods based on solubility differences. For example, isoelectric precipitation makes use of the alteration in protein solubility as a function of pH while fractionation with a solvent is based on the variation in protein solubility as a function of dielectric constant. Neutral salts, for example, ammonium sulfate, are employed to precipitate proteins due to decreased protein solubility based on high ionic strength of the salt. The drawback is that solvent fractionation can cause protein denaturation. Neither of these methods are capable of purifying proteins beyond a moderate level.

To avoid the negative elements of above techniques, affinity chromatography is often preferred. It is based on the ability of proteins to bind non-covalently but specifically with an immobilized ligand. When used alone, it can purify proteins from complex mixtures without significant loss. It requires the availability of the corresponding ligand for the desired protein; for example, an antibody for a protein antigen. It should be stressed that in some cases it may be difficult to obtain a specific ligand and such ligands do not exist for all proteins. As a result, this technique has not been applied as a universal method for protein purification.

To circumvent this limitation, recombinant DNA technology may be used to provide an affinity purification system where antibodies to a linker peptide may be used as an immunoaffinity ligand. This should provide a method that is capable of purifying recombinant proteins in one-step, using affinity chromatography, without sacrificing high yields. The Hopp patent relates to synthesis of a fusion peptide containing an antigenic linker peptide. The fusion peptide of Hopp is passed through a column containing immobilized antibodies which bind to the antigenic linker. Thus, the fusion protein may be isolated. The major drawbacks of this technique are that either the buffer conditions which are necessary to allow immunogenic complexing or the buffer conditions which must be present to terminate such complexes may denature the desired polypeptide product.

Immobilized Metal Ion Affinity Chromatography (IMAC) for fractionating proteins was first disclosed by Porath, I. et al., Nature 258:598–599 (1975). Porath disclosed derivatizing a resin with iminodiacetic acid (IDA) and chelating metal ions to the IDA-derivatized resin. Porath disclosed that proteins could be immobilized in a column which contained immobilized metal ions. The teachings of Porath include attaching a commonly used iminodiacetic acid (IDA) to a matrix followed by chelating a metal ion to the IDA-containing support resin. The proteins bind to the metal ion(s) through amino acid residues capable of donating electrons. Amino acids with potential electron donor groups are cysteine, histidines, and tryptophan. Proteins interact with metal ions through one or more of these amino acids with electron donating side chains. The actual mechanisms which result in binding of proteins to free metal ions or immobilized metal ions are not well known. A number of factors play a role; for example, conformation of the particular protein, number of available coordination sites on the immobilized metal ion, accessibility of protein side chains to the metal ion, number of available amino acids for coordination with the immobilized metal ion. Therefore, it is difficult to predict which protein will bind and with what affinity.

Smith et al. discloses in U.S. Pat. No. 4,569,794 that certain amino acids residues are responsible for the binding of the protein to the immobilized metal ions. However, if histidine side chains are involved in the binding the bound protein can be eluted by lowering the pH or using competitive counter ligands such as imidazole. Histidines containing di- or tripeptides in proteins have been used to show that IMAC is a specific and selective purification technique (U.S. Pat. No. 4,569,794). Accordingly, Smith et al. disclosed using recombinant DNA techniques to attach a metal chelating peptide to a desired polypeptide reproduced by recombinant techniques in order to provide a handle to the desired polypeptide. This handle can be used in protein purification by providing the chimeric protein with a metal chelating linker. Smith et al. disclosed several examples of metal chelating peptides, specifically those containing histidine, cysteine, methionine, glutamic acid, aspartic acid, lysine, and tyrosine. Smith et al. discloses that a fusion protein comprising a desired polypeptide with an attached metal chelating peptide handle may be purified from contaminants by passing the fusion protein and contaminants through columns containing immobilized metal ions. The fusion protein will chelate at the metal chelating peptide linker to the immobilized metal ions. The contaminants freely pass through the column and can thus be removed. By changing the conditions of the column, the chimerics can be released and then can be collected in pure form.

The present invention provides an improved method of purifying recombinant polypeptides and/or proteins. Recombinant polypeptides and proteins may be produced and purified by the method of the present invention with greater ease and therefore, more efficiently. Furthermore, these products may be recovered in pure, biologically active form. Using the method of the present invention, high yields of biologically active proteins may be efficiently recovered. The present invention also provides a method for removing the metal binding peptide from the purified chimeric protein without having to introduce a site-specific cleavage sequence.

The present invention is directed at the purification of biologically active recombinant polypeptides and/or proteins from bacterial or non-bacterial sources, most preferably those recombinant proteins expressed in a soluble form or secreted from the host as a fusion protein containing a metal chelating peptide. According to the present invention, the desired protein is first produced as a fusion protein which, in addition to the amino acid sequence of the desired protein, contains a linker peptide. The linker peptide of the present invention is a metal ion chelating peptide. Therefore, when the fusion protein according to the present invention is contacted with an immobilized metal ion containing resin, the fusion protein will be immobilized which will allow it to be separated from impurities.

It is possible to employ the commonly used IDA resin in IMAC for the purification of recombinant proteins having at least three alternating histidine residues. In a preferred embodiment of the invention, the amino acids that alternate with histidines are those which are specifically recognized by dipeptidylpeptidase I (DPP I). It is these discoveries that form the basis of this invention which is directed to fusion proteins comprising metal chelating affinity peptides, containing at least three alternate histidine residues, and a desired biologically active polypeptide or protein attached directly or indirectly to this/these metal chelating affinity peptides, a process for their synthesis by rDNA technology and a process for their purification by IMAC on commonly used IDA resins.

When the fusion protein is produced, the desired protein may be isolated and purified by passing the fusion protein through a column containing immobilized metal ions. The fusion protein chelates to the immobilized metal ions for a sufficient amount of time to allow it to be separated from other materials. The metal chelating peptides of the present invention provide superior and unexpected results over those taught or suggested by any of the prior art. The fusion protein of the present invention optionally contains a cleavage site that is located between the desired protein and the linker peptide and which is recognized by an endopeptidase. The purified fusion protein can then be cleaved at the scissile bond to separate the desired protein from the linker peptide. Alternatively, the metal chelating peptide according to the present invention may be removed from the desired protein portion by dipeptidylpeptidase I digestion.

The conditions needed in the purification step of the present method do not denature the fusion protein. The fusion protein may thus be purified to a biologically active final product in high yields using relatively few steps.

INFORMATION DISCLOSURE

U.S. Pat. No. 4,569,794 issued Feb. 11, 1986 to Smith et al. discloses a process for separating a biologically active polypeptide from impurities by producing the desired polypeptide as a fusion protein containing a metal ion chelating peptide linker. The present invention discloses metal chelating peptide linkers which provide superior results to those taught or suggested by Smith. Nothing in Smith teaches or suggests to one having ordinary skill in the an that peptide linkers according the present invention would provide such superior properties over the peptide linkers disclosed in Smith.

Australian Patent Application Document No. AU-A-12709/88 discloses fusion proteins which contain affinity peptides useful in IMAC. The affinity peptides disclosed contained at least two adjacent histidine residues. Australian patent AU-A-12709/88 discloses use of these affinity peptides in an IMAC purification process which requires special synthetic chemistry for making nitrilotriacetic acid (NTA) resins.

EP 0 163 573 discloses DNA sequences encoding peptides cleavable by renin and for the insertion of said sequences into plasmid vectors for the production of cleavable fusion proteins. This document discloses the use of a DNA sequence for a renin cleavable linker to connect genes for two polypeptides to form a chimeric gene which encodes a fusion protein. When expressed, the fusion protein may be separated into the substituent polypeptides using renin.

U.S. Pat. No. 4,782,137 issued Nov. 1, 1988 to Hoppet al., discloses the synthesis of a fusion protein having a highly antigenic N-terminal portion and a desired polypeptide at the C-terminal portion. According to Hoppet al., the fusion proteins are purified from crude supernatent by passing crude supernatent through a column containing immobilized antibodies which recognize the antigenic N-terminal portion of the fusion protein. The immobilized antibodies immobilize the protein in the column while the undesired components of the supernatent are eluted. The column conditions can then be changed to eliminate the affinity conditions and cause the antigen-antibody complex to dissociate. The fusion protein is then eluted and collected. Another drawback to Hoppet al. is that the conditions which allow for the affinity complexing and/or those which eliminate antibody-antigen recognition may cause denaturation of the fusion protein and loss of bioactivity of the desired protein.

U.S. Pat. No. 4,751,180 issued Jun. 14, 1988 to Cousens et al., discloses methods of producing a desired protein product by expression of a fusion gene. The expression of a desired gene linked with a gene which encodes a protein product normally produced in a very large amount in the host is disclosed. The two genes are linked with the DNA sequence which encodes a cleavable amino acid sequence. Thus, after the fusion protein is produced and purified, the desired protein may be separated from other protein at the clearable linker.

Smith, M. C., et al., J. Biol. Chem. Vol. 263, 15:7211–7215 (1988) disclose experimental results supporting the hypothesis that specific metal chelating peptides on the $NH_2$ terminus of a protein can be used to purify that protein using metal ion affinity chromatography. This reference provides specific data regarding one of the examples in the above-described U.S. Pat. No. 4,569,794. Specifically, the use of the metal chelating peptide His-Trp linked to either leutenizing hormone-releasing hormone or proinsulin allows the chimeric peptide to be purified using IMAC whereas control molecules not containing the His-Trp linker cannot be recovered in the like manner.

Hochuli, E. et al., J. Chromat. 411:177–184 (1987) disclose a nitrilotriacetic acid absorbent useful for metal chelate affinity chromatography. It is reported that the disclosed absorbent when charged with $Ni^{2+}$ is useful in binding to peptides and proteins containing neighboring histidine residues.

Ljungquist, C. et al., Eur. J. Biochem. 186:563–569 (1989) disclose the use of the metal chelating peptide Ala-His-Gly-His-Arg-Pro in multiplicities of four and eight together with a column containing immobilized $Zn^{2+}$ ions. According to Ljungquist use of this metal chelating peptide with zinc columns does not provide purification of the fusion proteins. According to this reference, even two copies of the linker (Ala-His-Gly-His-Arg-Pro-Ala-His-Gly-His-Arg-Pro), fused to the 5' end of a gene coding for β-galactosidase, showed little or nor binding to immobilized gene.

Haffey, M. L. et al., DNA, Volume 6, 6:565–571 (1987), disclose a synthetic oligonucleotide that codes for an amino acid sequence specifically recognized and cleaved by renin. Haffey et al. teach that oligonucleotide may be inserted into a plasmid expression vector between two genes which encode desired proteins. Expression of the two genes linked with the oligonucleotide results in a fusion peptide which may be cleaved by renin. This publication corresponds to EP 0 163 573 described above.

Hopp, T. P. et al., Bio/Technol. 6:1204–1210, October 1988, disclose addition of an eight amino acid peptide to the N-terminus of a desired recombinant lymphokine in order to provide a antigenic N-terminus which can be used in immunoaffinity purification. This publication corresponds to U.S. Pat. No. 4,782,137 described above.

Kreil, G., TIBS 15:23–26 (January 1990) reviews of the stepwise cleavage of dipeptides by dipeptidypeptidases (DPP's) in the conversion of precursors to final products.

Dalboge, H., et al, Bio/technology, 5:161–164 (February 1987) disclose converting E. coli produced precursor of human growth hormone (hGH) to authentic hGH in vitro. The N-terminal extension of the precursor is removed by DAP I (dipeptidylpeptidase or DPP I).

Dalboge, H., et al, FEBS, Vol. 246 (1,2):89–93 (March 1989) disclose the cloning and expression of IL-1β precursor and its conversion to IL-1β by removal of the precursor's N-terminal extension using DPP I.

Dalboge, H., et al, FEBS, Vol. 266 (1,2):1–3 (June 1990) refer to in vivo processing of N-terminal methionine in E. coli. It is reported that the removal of the N-terminal methionine from extended human growth hormone was dependent upon the amino acid adjacent to the methionine.

McDonald, J. K. et at., J. Biol. Chem. Vol. 244(10):2693–2709 (May 25, 1969) refers to new observations in the substrate specificity of DPP I.

SUMMARY OF THE INVENTION

The present invention relates to fusion proteins which comprise a biologically active polypeptide or protein portion and metal chelating peptide. The fusion proteins of the present invention contains metal chelating peptides which have alternating histidine residues. Metal chelating peptides according to the present invention comprise at least three and preferably six alternating histidine residues which are separated from each sequentially linked residue by a non-histidine residue.

The present invention provides a method of purifying a desired polypeptide comprising the steps of collecting a fusion protein comprising a metal chelating peptide linker through a column containing immobilized metal ions.

Furthermore, the present invention provides a kit for purifying a desired polypeptide comprising: a DNA molecule containing a DNA sequence which encodes a metal chelating peptide wherein the DNA molecule is used to construct a chimeric gene comprising a gene which encodes a desired polypeptide fused with the DNA sequence which encodes a metal chelating peptide; and, a column containing immobilized metal ions, wherein the column is used to harvest fusion polypeptide products produced by expression of the chimeric gene in a transformed cell by passing the products through a column containing immobilized metal ions.

DETAILED DESCRIPTION OF THE INVENTION

The present invention relates to the purification of biologically active recombinant polypeptides and/or proteins produced by transformed host cells. The desired biologically active recombinant proteins are most preferably produced in a soluble form or secreted from the host. According to the present invention, the desired biologically active protein is expressed as a fusion protein containing a metal ion chelating peptide that can be immobilized by an immobilized resin that contains metal ions. The fusion protein is purified from the material present in the secretion media or extraction solution it is contained in by contacting the secretion media or extraction solution with the metal ion resin. A proteolytic cleavage site may be optionally interposed between the portion of the fusion protein which contains the desired protein and the peptide linker whereby an enzyme capable of cleaving the fusion protein at the recognition site can be used to separate the components. Moreover, optionally, the peptide linker portion of the fusion protein is a substrate for dipeptidlypeptidase (DPP) digestion, specifically DPP I. The DPP I can be added to the purified fusion protein to remove the peptide linker portion and thereby produce the desired protein.

The desired proteins which are produced by recombinant DNA technology and purified are expressed as a fusion protein. The fusion protein is produced by host cells transformed with the genetic information encoding the fusion protein. The host cells may secrete the fusion protein into the culture media or store it in the cells whereby the cells must be collected and disrupted in order to extract the product. As hosts, both E. coli and mammalian cells are preferred hosts. Of these two, E. coli is the preferred host according to this invention.

The culture media containing the secreted fusion protein or the cell extracts containing the fusion protein are passed through a column that contains an immobilized resin comprising a metal ion. The preferred metal ions are copper, zinc, cobalt, and nickel; nickel being the most preferred. All of the components of either solution freely pass through the column except the fusion protein. The immobilized resin chelates the peptide linker and, therefore, impedes the movement of the fusion protein through the column. Thus, all the impurities are eluted through the column except the fusion protein. The conditions in the column can then be changed so that the resin releases the fusion protein which can then be collected. The bound chimeric protein molecules could be eluted by pH change, imidazole, or competition with another linker peptide from the IMAC column, and the chelating peptide cleaved from the chimeric protein by site specific proteolysis, thus releasing the highly purified protein molecule.

It is to be appreciated that some polypeptide or protein molecules will possess the desired enzymatic or biological activity with the metal chelate peptide still attached either at the C-terminal end or at the N-terminal end or both. In those cases the purification of the chimeric will be accomplished after the IMAC column, without subjecting the protein into site-specific proteolysis or DPP I cleavage.

The purification process of the present invention can be used batchwise or in continuously run columns.

If provided with an interposed cleavage site, the fusion protein can be separated into its components using the proteolytic enzyme or chemical cleavage means to cleave it at the scissile bond. The enzymatically clearable linker peptide is characterized by being able to undergo site-specific proteolysis. Alternatively, a metal chelating linker peptide may be provided which is optionally a DDP I substrate.

Suitable preferred cleaving enzymes in accordance with this invention are thrombin, enterokinase, factor Xa, human renin, DPP I, DPP II, DPP IV, and carboxylpeptidase A. Most preferred of these enzymes according to this invention is recombinant human renin and DPP I. Chemical cleavage based on Met, Asp-Pro, and Asn-Gly are recommended. Of these, Met is the most preferred one.

After the cleavage reaction occurs, the desired protein is generated from the fusion protein. These desired proteins may be recovered using simple techniques well known to those having ordinary skill in the art.

The terms "fusion protein" and "chimeric proteins" as used herein are interchangeable and refer to polypeptides and proteins which consist of one or two metal ion chelating linker peptides and a biologically active polypeptide or protein or a short peptide linked directly or indirectly to the linker peptides.

The term "desired polypeptide" used herein refers to a biologically active polypeptide or protein.

The terms "metal ion chelating peptide", "metal binding peptide" and "linker peptide" are used interchangeably to refer to an amino acid sequence which displays an affinity to metal ions. The minimum length of the immobilized metal ion chelating peptide according to the present invention is six amino acids including three alternating histidines. The most preferred length is twelve amino acids including six alternating histidines.

The term "enzyme" referred to herein in the context of a cleavage enzyme means a polypeptide or protein which recognizes a specific amino acid sequence in a polypeptide and cleaves the polypeptide at the scissile bond. In the preferred embodiment of the present invention, human renin is the enzyme which is used in the immobilized enzyme column. In another embodiment, DPP I is the enzyme. DPP I cleaves its substrate by removing two amino acids at a time from the N-terminus.

The terms "cleavage site" used herein refers to an amino acid sequence which is recognized and cleaved by an enzyme or chemical means at the scissile bond.

The term "scissile bond" referred to herein is the juncture where cleavage occurs; for example the scissile bond recognized by human renin may be the Leu-Leu bond or the Leu-Val bond in the linker peptide or affinity peptide.

The term "dipeptidylpeptidase I substrate" refers to an amino acid sequence which is free of Proline residues and does not contain Arginine or Lysine residues at odd numbered positions.

The term "odd numbered positions" refers to the amino acids residues occupying odd numbered sites on the amino acid sequence of a peptide. The odd numbered positions are determined from the N-terminus of the peptide and comprise amino acids 1, 3, 5, . . . etc.

The present invention may be used to purify any prokaryotic or eukaroytic protein that can be expressed as the product of recombinant DNA technology in a transformed host cell. These recombinant protein products include hormones, receptors, enzymes, storage proteins, blood proteins, mutant proteins produced by protein engineering techniques, or synthetic proteins.

The chimeric proteins of this invention are prepared by recombinant DNA methodology. In accordance with the present invention, a gene sequence coding for a desired protein is isolated, synthesized or otherwise obtained and operably linked to a DNA sequence coding for the linker peptide. The hybrid gene containing the gene for a desired protein operably linked to a DNA sequence encoding a linker peptide is referred to as a chimeric gene.

The chimeric gene is inserted into an expression vector which allows for the expression of the desired chimeric protein in a suitable transformed host. The expression vector provides the inserted chimeric gene with the necessary regulatory sequences to control expression in the suitable transformed host.

There are six elements of control expression sequence for proteins which are to be secreted from a host into the medium, while five of these elements apply to chimeric proteins expressed intracellularly. These elements in the order they appear in the gene are: a) the promoter region; b) the 5' untranslated region; c) signal sequence; d) the chimeric coding sequence; e) the 3' untranslated region; f) the transcription termination site. Fusion protein which are not secreted do not contain c), the signal sequence.

Methods and materials for preparing recombinant vectors and transforming host cells using the same, replicating the vectors in host cells and expressing biologically active foreign polypeptides and proteins are described in Principles of Gene Manipulation, by Old and Primrose, 2nd edition, 1981 and Maniatis et al., Molecular Cloning, Cold Spring Harbor Laboratory 1982, both incorporated herein by reference.

In addition to the genetic information necessary to encode and produce the fusion peptide, a column containing an immobilized resin is provided. Immobilized resins used in the present invention are well known in the art.

Additionally, the present invention relates to genes which encode fusion proteins, expression vectors containing the same, microorganisms transformed with these expression vectors, and process for obtaining these genes, expression vectors, and microorganisms transformed with said vectors.

According to the present invention, the metal ions may be copper, nickel, cobalt, or zinc. According to the present invention, the desired polypeptides produced may include HIV-1 RNase H, tPA, IL-1, BST, IL-1 receptor, CD4, HIV RT, human nerve growth factor, sCD4-PE40, human respiratory syncytial virus (RSV) FG chimeric glycoprotein, and PE40.

The metal ion chelating linker peptides in accordance with this invention are defined by the general formula:

$R_1$-(His-X)$_n$-$R_2$ where $R_1$ is a hydrogen atom, an amino acid, a sequence of few amino acids, a sequence of several amino acids, or a polypeptide. $R_2$ represents a desired polypeptide; n=3 to 6, and X is selected from the following amino acids Asp, Pro, Glu, Ala, Gly, Val, Ser, Leu, Ile, and Thr or a combination of any of these.

A preferred sub-class of the above is Asp, Glu, Pro. Of these, Asp and Pro are most preferred.

In the preferred embodiment of the present invention, the metal ion chelating linker peptides in accordance with this invention are defined by the general formula:

Pro-Ile-His-X-His-X-His-X-$R_2$

In the preferred embodiment of the present invention, a column is provided that contains immobilized resin made up of nickel ions which recognizes the above described linker peptides.

Optionally, a cleavage site may be interposed between the linker peptide and desired protein portions of the fusion peptide. In the preferred embodiment of the present invention, the cleavage site that is located between the desired protein and the linker peptide and which is recognized by human renin is interposed between the linker peptide and the desired protein. In yet another embodiment of the invention, the cleavage site is provided by residues alternating with histidines and DPP I is the enzyme used to release the desired polypeptide.

In another embodiment, $R_1$ may be a second desired polypeptide or a polypeptide which drives expression. If $R_1$ is a second desired polypeptide it may have a cleavage site interposed between it and the linker peptide. Alternatively it may not and the first desired peptide may also not have a cleavage site adjacent thereto. This type of arrangement is particularly useful when chimeric proteins are constructed which comprise epitopes from two portions of antigenic protein or from two different antigenic proteins. Such chimeric proteins are useful in vaccine preparations.

As noted above, an $R_1$ may be a protein which drives expression. It is well known that the presence of some proteins in a cell result in expression of genes. If a chimeric protein contains an active portion of the protein which prompts or enhances expression of the gene encoding it, greater quantities of the protein may be expressed than if it were not present.

In another embodiment of the present invention, the peptide linker portion is a dipeptidylpeptidase I substrate, that is it does not contain any Proline residues Accordingly, in a fusion protein according to this embodiment of the present invention, R1 does not comprise Pro and X is not Pro. In the preferred form of this embodiment, the 2nd or 3rd amino acid of the desired protein is Proline since DPP I is unable to digest if Proline is involved in a cleavage site. Thus, when the entire peptide linker portion is removed, digestion by DPP I will stop and the complete desired protein will be left.

DESCRIPTION OF THE PREFERRED EMBODIMENTS

Example 1 Construction of Fusion Proteins which Contain HIV Reverse Transcriptase A strategy to purify chimeric proteins from recombinant *E. coli* is described based on metal binding peptide domains containing alternate histidines, with affinity for an immobilized metal ion. A renin cleavage site was introduced between the metal binding peptide and the desired protein in order to release the metal binding peptide after purification. Vectors were constructed to direct the synthesis of fusion proteins using HIV reverse transcriptase (RT) as the model protein. As shown below, two fusion proteins (#1 and/#2) were designed to possess alternating histidines for purification by immobilized metal ion affinity chromatography (IMAC). Two control fusion proteins (#3 and #4) without the metal binding peptide were also included.

1) Pro-Ile-His-Asp-His-Asp-His-Pro-Phe-His-Leu-Val-Ile-His-Ser-RT
2) Pro-Ile-His-Asp-His-Asp-His-Pro-Phe-His-Leu-Leu-Tyr-Tyr-Ser-RT
3) Pro-Ile-Pro-Phe-His-Leu-Val-Ile-His-Ser-RT
4) Pro-Ile-Pro-Phe-His-Leu-Leu-Tyr-Tyr-Ser-RT

These fusion proteins were cloned and expressed in *E. coli*, and were purified using DEAE chromatography and RP-HPLC. Both N-terminal sequencing and ELISA utilizing antibodies to the metal binding peptide were used to characterize the fusion protein proteins before and after renin cleavage. Application of the alternating histidine-containing fusion proteins to the purification of recombinant proteins by IMAC was also performed.

We first cloned, expressed, and characterized a number of fusion proteins containing alternating histidines at the amino terminus. General laboratory chemicals were purchased from the Sigma Chemical Co. Electrophoresis reagents were obtained from Bio-Rad Laboratories. Poly rA:oligo dT, dTTP were obtained from Pharmacia-LKB. [$^3$H]dTTB was obtained from New England Nuclear-Corp./Dupont and diluted with cold dTTB to provide a final specific activity of 140 CBM/pmole. No additional purification of this deoxynucleotide was required. Glass microfibre filters (GF/C) were purchased from Whatman, Maidstone, England. Microtiter plates were purchased from Costar, Cambridge, Mass. HPLC was purchased from Varian Instruments Walnut Creek, Calif. The RP-HPLC column was purchased from Anspec Company, Inc. Ann Arbor, Mich. Sequencing chemicals and instrumentation were purchased from Applied Biosystems.

Construction of Chimeric Genes Containing HIV RT Gene

All recombinant DNAs were prepared by standard techniques. Construction of expression vectors encoding HIV RT-containing fusion proteins was performed as follows. The oligonucleotides corresponding to the metal binding peptide and/or renin cleavage sequence were constructed from the 10 oligonucleotides shown below.

1. 5' AA TTC ATG CCC ATT CAC GAT CAC GAT CAC CCC TTT CAC TTA GTA ATT CAC AGC CCC ATT AGC CCT 3'
2. 5' ATT GAG ACT GTA CCA GTA AAA TTA AAG CCA GGA ATG GAT GGC CCA AAA GTT AAA CAA TGG 3'
3. 5' CT AAT GGG GCT GTG AAT TAC TAA GTG AAA GGG GTG ATC GTG ATC GTG AAT GGG CAT G 3'

4. 5' CCA TTG TTT AAC TTT TGG GCC ATC CAT TCC TGG CTT TAA TTT TAC TGG TAC AGT CTC AAT AGG G 3'
5. 5' AA TTC ATG CCC ATT CAC GAT CAC GAT CAC CCC TTT CAC TTA CTA TAC TAC AGC CCC ATT AGC CCT 3'
6. 5' CT AAT GGG GCT GTA GTA TAG TAA GTG AAA GGG GTG ATC GTG ATC GTG AAT GGG CAT G 3'
7. 5' AA TTC ATG CCC ATT CCC TTT CAC TTA GTA ATT CAC AGC CCC ATT AGC CCT 3'
8. 5' CT AAT GGG GCT GTG AAT TAC TAA GTG AAA GGG AAT GGG CAT G 3'
9. 5' AA TTC ATG CCC ATT CCC TTT CAC TTA CTA TAC TAC AGC CCC ATT AGC CCT 3'
10. 5' CT AAT GGG GCT GTA GTA TAG TAA GTG AAA GGG AAT GGG CAT G 3'

Purification, annealing and ligation of oligonucleotides:

All of the above oligonucleotides were purified using polyacrylamide gels. The purified oligonucleotides were annealed and ligated in the following formats.

Construction #1
5'oligo #1-3'5'-oligo #2-3' 3'-oligo #3-5'3'-oligo #4-5'
Construction #2
5'-oilgo #5-3'5'-oligo #2-3' 3'-oligo #6-5'3'-oligo #4-5'
Construction #3
5'-oligo #7-3'5'-oligo #2-3' 3'-oligo #8-5'3'-oligo #4-5'
Construction #4
5'-oligo #9-3'5'-oligo #2-3' 3'-oligo #10-5'3'-oligo #4-5'

Constructions #1 and #3 contained the human renin cleavage sequence. Constructions #2 and #4 contained the rat renin cleavage sequence. The above constructions were built to contain the following restriction sites:
5'EcoR1-3' 3'-5'Bal I To prepare expression vectors encoding alternate histidines/renin cleavage sequence/HIV RT we ligated the above oligonucleotides as EcoR1/Bal I pieces into the final expression vector as 1 part of a three-way ligation. The other two pieces were prepared as follows. A 1.5 Kb EcoR1/Bal I linearized fragment of the vector called TM-3, which contained the majority of the HIV RT open reading frame. A 4.55 Kb EcoR1/Hind III linearized fragment of pKK223-3 was then purified on agarose gels and mixed with the EcoR1/Bal I fragment of TM-3 and either of the four ligated sets of oligonucleotides constructed above.

Expression vectors containing the chimeric gene constructs were used to transform E. coli by standard techniques. Expression of the genes in E. coli resulted in the production of the fusion proteins encoded by the chimeric genes. These fusion proteins consisted of the two N-terminal HIV RT amino acids (Pro-Ile), followed by alternate histidines (metal binding peptide), renin cleavage sequence, and ended with the entire HIV RT. For control constructs 3 and 4, the fusion proteins lack the N-terminal alternate histidines and start with the Pro-Ile of the HIV RT, followed by the renin cleavage sequence and the entire HIV RT.

Preparation of Crude E. coli Extracts

Approximately 3 g of E. coli cell paste was suspended in 30 ml of 0.25M potassium phosphate, pH 7.2 containing 1 mM dithiothreitol (DTY), EDTA, phenylmethylsulfonyl fluoride (PMSF), and benzamidine HCL, 10 mg/liter aprotinin, leupeptin, and bestatin. This suspension was passed through a French Press three times to break the cells. Cell lysates were centrifuged at 12,000 rpm for 1 hr. The supernatant was removed and solid ammonium sulfate added to 70% saturation. After stirring for 1 hr, the suspension was centrifuged at 12,000 rpm for 1 hr. The supernatant was discarded and the pellet was redissolved in 2.25 mls of 50 mM Tfis pH 7.5 containing 1 mM DTT, PMSF, and benzamidine. The solution was then dialyzed overnight in 20 mM Tris, 50 mM NaCl, 1 mM DTT, 10% glycerol, and 0.1 mM EDTA pH 7.5 (Buffer A) at 4° C. The dialysate was collected, diluted with one volume of Buffer A, and applied to a 10 ml column of washed DEAE cellulose equilibrated in Buffer A. The run through was collected batchwise and the column further washed with 50 mls of Buffer A. These solutions were collected, pooled, and concentrated by 70% ammonium sulfate precipitation and resuspended in 2 mls of Buffer A and dialyzed as described above. Concentrated RT was stored in Buffer A at −20° C.

Samples were analyzed by assaying RT activity and SDS-PAGE. SDS-polyacrylamide gel electrophoresis was done using 11% or 9% gels run according to the procedure of Laemmli and stained with Commassie G-250. SDS-PAGE of chimerics #1 and #2 shows that for chimeric #1 or chimeric #2 a major band corresponding to the expected molecular weight of 66 Kd was observed after the DEAE purification step. Most of the E. coli contaminating proteins were eliminated as judged by comparison of lanes containing purified material with a lane containing the crude E. coli extract. The DEAE purified material was, however, not suitable for sequence analysis and therefore further purification was carried out using HPLC.

HPLC purification of DEAE purified material

DEAE purified samples were further purified using HPLC. Chromatography was done using a 0% to 70% gradient of 0.1% TFA:H2O to 0.1% TFA:ACN in 40 min; peaks were detected at 215 nm at a flow rate of 1.0 ml/min. Peaks were collected manually, dried in a Speed-Vat, and prepared for sequencing as described in the next section. The HPLC peaks of chimerics #1 and #2 were further analyzed by SDS-PAGE and N-terminal sequence analysis.

SDS-PAGE and Sequencing of HPLC Purified Chimerics #1 and #2

HPLC purified chimerics were subjected to SDS-PAGE which showed that HPLC resulted in purification of the chimerics while removing other contaminating proteins observed after the DEAE step. Two control chimerics without the metal binding peptides chimeric #3 and chimeric #4, were purified by DEAE chromatography followed by HPLC.

N-Terminal Sequence

Using N-terminal sequence analysis, the observed sequence was compared to the expected sequence for each fusion protein. Sequence analysis was performed on an Applied Biosystems (ABI) 470A sequencer equipped with an on-line ABI 120A PTH analyzer. Cartridge filters were prepared with 1.5 mg polybrene using the ABI program 03RPRE. HPLC purified samples were dissolved in 75 µl of 50% acetic acid and loaded onto the filter in three aliquots. Sequencing was done by using the ABI program 03RPTH.

It was confirmed that the chimerics #1 and #2 possess the correct N-terminal sequence up to and through the renin cleavage site. Likewise, the N-terminal sequence analysis of control chimerics #3 and 4 was carried out after HPLC purification. As expected, N-terminal methionine was removed in each case.

Example 2 Effect of HIV RT and Metal Binding Peptide on the Cleavage by Human Renin Chimeric #1 and Chimeric #3 contain the sequence (HPF-HLVIH) required for cleavage by human renin at the Leu-Val bond. Therefore, the DEAE purified chimeric #1 and chimeric #3 were dialyzed into 150 mM Na2HPO4, 160 mM NaCl, 1 mM PMSF pH 6.0 and incubated with or without renin.(substrate: enzyme ratio of 30: 1) for 2 hrs at 37° C. Cleavage of the metal binding peptide from the RT was accomplished by incubating 300 µg of DEAE purified chimeric with 10 µg of renin for 2 hrs at 37° C. followed by chromatography on a 4.6 mm×15 cm, 300A pore size C-4 (Vydac) RPHPLC column. The cleaved product was isolated by HPLC for chimeric #1. Final characterization was carried out by N-terminal sequence analysis. Results of renin cleavage assays for chimeric #1 and chimeric #3 show that the N-terminal was Val and the remaining sequence matched with what was expected after cleavage at the Leu-Val bond. These results confirm that human renin-specific sequence flanked by a metal binding peptide and HIV RT is fully accessible. The metal binding peptide or HIV RT has no effect on the ability of human renin to specifically cleave at the Leu-Val.

Example 3 Effect of N-Terminal Peptide Linker on RT Activity

The HIV-RT-containing chimeric proteins expressed in E. coli displayed RT activity despite the presence of a N-terminal peptide linker. In the case of chimeric #1, we compared RT activity before and after renin cleavage performed on freshly prepared crude E. coli lysates. Reverse transcriptase activity was assayed by measurement of [$^3$H] dTMP incorporation into a synthetic template-primer with the following modifications: A 15 µl aliquot of the appropriate enzyme solution was added to each well of a half/area 96 well microliter plate followed by 60 µl of stock 8 part assay solution made by mixing 100 µl each of 10 mM DTT, 0.5 M Tri$_s$ HCl pH 8.0, 50 mM MgCl$_2$, 0.8 M KCl, dTTP 2.5 mM radiolabelled, and poly rA:oligo 5 U/ml with 200 µl H$_2$O. At appropriate time intervals, generally 5–20 min. at 25° C., three 20 µl aliquots were removed and spotted individually onto ½×¾" glass fiber paper squares (GF/C) which were immediately dropped into a cold solution of 5% (w/v) trichloroacetic acid (TCA), processed, and counted. The activity before and after removal of the fusion by human renin was not significantly distinguishable. The renin cleavage in crude extracts containing chimeric #1 was confirmed by using an ELBA specific for the metal binding peptide. HIV RT was used as an internal control to ensure that human renin has no effect on the activity of HIV RT. It was concluded that the N-terminal fusion, at least in the case of chimeric #1, does not appear to have decreased the biological activity of HIV RT. It should be noted that similar studies with chimeric #2 were not feasible due to the presence of the rat sequence which is known to be a very poor substrate for human renin.

Example 4 Construction of β-Galactosidase Containing Fusion Protein

A strategy to purify chimeric proteins from recombinant E. coil is described based on metal binding peptide domains containing alternate histidines, with affinity for an immobilized metal ion. Vectors were constructed to direct the synthesis of fusion proteins using β-galactosidase as the model protein. As shown below, these fusion proteins were designed to possess alternating histidines for purification by immobilized metal ion affinity chromatography (IMAC). The following formula, #5, represents the fusion protein constructed.

5) Pro-Ile-His-Asp-His-Asp-His-Pro-Phe-His-Leu-β-galactosidase

The oligonucleotides corresponding the alternate histidine linker region of the β-galactosidase construct are shown below;

5' AATTC ATG CCC ATT CAC GAT CAC GAT CAC CCC TTT CAC TTA 3' 3' G TAC GGG TAA GTG CTA GTG CTA GTG GGG AAA GTG AAT GATC 5'

This set of oligonucleotides was annealed and ligated using standard DNA techniques. It was then cloned into the EcoR1/XbaI sites of pUC18. This plasmid was restricted with EcoR1/Pvu2 and the assembled oligo region containing 33 bp of pUC18 at the 3' end was isolated after gel electrophoresis. This fragment was then cloned into the EcoR1/Pvu2 sites of TM-9. This latter plasmid carries the entire B-galactosidase gene in pKK223-3.

The plasmids were transformed into the JM109 strain of E. coli, grown on ampicillin containing plates, clones were selected and sequenced using $^{32}$P dATP.

Purification and Characterization of β-Galactosidase-Containing Chimeric #5 from Recombinant E. coli This chimeric contained the metal binding peptide along with a stretch of renin-specific sequence up to the cleavage point. This was purified from crude E. coli lysate by immunoaffinity chromatography. The chimeric #5 containing β-galactosidase was purified using a modified procedure from that in the Cappel Technical Data Sheet provided with the column. A 1 ml column of immobilized IgG rabbit anti β-galactosidase Sepharose 4B was washed with 10 ml of 0.02M PBS, pH 7.3. E. coli extract of chimeric #5 was prepared as above. The sample was then dialysed in the above buffer and 1 ml aliquot was applied to the column. The column was then washed with 5 ml of above buffer and eluted with 8M urea. Urea-containing fractions were dialyzed and analyzed by SDS-PAGE. The material isolated from this column was analyzed by SDS-PAGE. The β-galactosidase chimeric protein appeared at the expected molecular weight. The presence of the metal binding peptide was confirmed by ELISA using antibodies to a peptide containing residues from the metal binding peptide.

Example 5 Purification of Fusion Proteins Using IMAC

The feasibility of using a metal binding peptide for the purification of recombinant proteins from crude extracts has been demonstrated by using the following chimerics expressed in recombinant E. coli with HIV reverse transcriptase (RT) or β-galactosidase as the model protein.

1 Pro-Ile-His-Asp-His-Asp-His-Pro-Phe-His-Leu-Val-Ile-His-Ser-RT
2 Pro-Ile-His-Asp-His-Asp-His-Pro-Phe-His-Leu-Leu-Tyr-Tyr-Ser-RT
3 Pro-Ile-Pro-Phe-His-Leu-Val-Ile-His-Ser-RT
4 Pro-Ile-Pro-Phe-His-Leu-Leu-Tyr-Tyr-Ser-RT
5 Pro-Ile-His-Asp-His-Asp-His-Pro-Phe-His-Leu-β-galactosidase Chimerics #3 and #4, lacking the metal binding peptide (mbp), were used as controls. In addition, HIV RT expressed in E. coli without the mbp and renin cleavage site was also included in this study for comparison purposes.

Separation of HIV RT from mbp-HIV RT (chimeric #1) Using Crude E. coli Extracts

The preparation of the cell extracts for use on IMAC columns required only a few short steps. The cell paste was suspended in 10 volumes of extract buffer and stirred at 4° C. for at least 1 hour. The extract buffer was composed of 20 mM Tris pH 8.0 containing 500 mM NaCl, 1 mM PMSF (phenylmethylsulfonyl fluoride), 1 mM benzamidine, 10 mg/L leupeptin, 10 mg/L aprotinin, and 10 mg/L bestatin. The suspension was passed through a French Press three times to insure breakage of the cells. The cell lysates were again stirred for 1 hour at 4° C. followed by centrifugation for 1 hour at 12,000 rpm, 4° C. The supernatant was stored at −20° C. and the pellet was discarded.

Initially, we studied the IMAC behavior of chimeric #1 on immobilized nickel. Immobilized metal affinity columns were prepared as follows. Chelating Sepharose Fast Flow from Pharmacia was washed thoroughly with Milli-Q water on a scintered glass filter. The gel was then resuspended in water to form a slurry. The slurry was poured carefully into a glass column (Pharmacia) to a volume of 6 mls (1×7 cm). After the gel had settled, the column was washed with 5 volumes of 50 mM EDTA (ethylenediaminetetraacetic acid) pH 8.0. Following this, the column was washed with 5 volumes of 0.2N NaOH and 5 volumes of Milli-Q water: The column then was charged with 5 volumes of 50 mM $NiSo_4$ (or $ZnCl_2$ or $CuSO_4$). Finally, the column was washed with 5 bed volumes of equilibration buffer. The equilibration buffer was made up of 20 mM Tris pH 8.0, containing 500 mM NaCl, 1 mM PMSF, 1 mM benzamidine, 10 mg/L leupeptin, and 10 mg/L aprotinin.

The column had been equilibrated with at least 5 volumes of equilibration buffer. 5–10 mls of crude recombinant *E. coli* extract were applied to the column by gravity. After all the crude material had entered the column, the column was washed with 10 column volumes of equilibration buffer containing 1.0M NaCl, instead of 500 mM NaCl, pH 8.0.

The column was then eluted with increasing concentrations of imidazole in the equilibration buffer at pH 8.0. For the earlier experiments, a large number of elutions were performed for each experiment to determine the concentration at which the chimeric eluted. Later this elution was simplified and usually just three imidazole concentrations were used: 35 mM, 100 mM, and 300 mM imidazole in the equilibration buffer, pH 8.0. Ten bed volumes of each imidazole buffer were used. Between elutions, the column was washed with 10 volumes of equilibration buffer. Finally, the column was stripped with 5 bed volumes of 50 mM EDTA pH 8.0 to determine if any protein was still bound to the column. The flow rates for the columns were 1.0 ml/min. 5 ml fractions were collected. The columns were run at room temperature.

Pierce protein assays were run to determine the protein content of the samples. This assay is an adaptation of the Bradford method and can detect protein concentrations as low as 1 μg/ml. A standard curve was constructed using purified BSA from Pierce with concentrations ranging from 1 to 30 μg/ml. One milliliter of standard or unknown was pipetted into a 16×100 mm test tube. One milliliter of Protein Assay Reagent was added to each tube and the tubes were vortexed. The absorbencies were read at 595 nm on a Bausch & Lomb Spectronic 2000. All the samples were done in duplicate. The assays were also done in a microtiter plate using 100 μl of sample and 100 μl of assay reagent. The results from the assay done in the microtiter plate were identical to those done in larger tubes.

Only a trace amount (5.8%) of applied RT activity was recovered in the fractions obtained by elution at 35 mM imidazole. Reverse Transcriptase activity was determined by the measurement of [$^3$H] dTMP incorporation into a synthetic template primer. Typically, in our assays 15 μl of a sample were placed in a well of a half area microtiter plate. 60 μl of stock 8 part assay solution was added to each well while the plate was on ice. The plate was then shaken gently for 20 minutes at room temperature and 25° C. The plate was again placed on ice. Three 20 μl aliquots were spotted individually onto Whatman GF/C paper (½×¾" pieces) and immediately dropped into ice-cold 5% TCA. The papers were washed three times in 5 % TCA followed by two washings in 95% EtOH. The washings lasted 5 minutes each. The papers were then washed twice in anhydrous ethyl ether for 2 minutes per wash. The washings, except for the ether wash, were done on ice. The beaker was swirled continuously while the papers were being washed. The papers were then dried, added to scintillation vials, and counted for tritium. The major activity peak eluted at a 100 mM imidazole concentration and accounted for 87% of the total activity recovered. Thus, elution of chimeric #1 from HIV RT was remarkably different and this prompted us to carry out separation of HIV RT from chimeric #1 by mixing crude *E. coli* extracts prior to the IMAC experiments described below.

The elution profile of a mixture of HIV RT and mbp-HIV RT using crude *E. coli* extracts show most of the *E. coli* contaminating proteins passed through unretarded. HIV RT along with contaminating *E. coli* proteins was eluted at 10 mM, as determined by RT activity assay and SDS-PAGE. At 30 mM and 50 mM imidazole, trace amounts of RT activity were eluted, while most of the remaining bound chimeric #1 activity was eluted at 100 mM imidazole.

The highest RT activity fraction from each major peak was analyzed by ELISA using polyclonal antibodies to the mbp. The fraction from the 10 mM imidazole peak showed no cross-reactivity in the ELISA against two different bleedings taken from two different rabbits. In contrast, the fraction from the 100 mM imidazole peak was positive in the ELISA. These studies confirm that the earlier peak is the HIV RT peak while the later activity peak is due to the mbp-containing HIV RT. SDS-PAGE of various fractions across these activity peaks show fractions eluted with 100 mM were devoid of protein contaminants which were observed in the fractions eluted with 35 mM imidazole. It was concluded that mbp-HIV RT is retarded on the Chelating Sepharose-$Ni^{++}$ column much more strongly due to the presence of histidines in the mbp. This strong and specific binding of chimeric #1 was abolished when the mbp was removed from the chimeric with human renin prior to the IMAC step.

When the crude chimeric protein lacking the mbp (construct #3), Pro-Ile-Pro-Phe-His-Leu-Val-Ile-His-Ser-RT, but retaining the corresponding renin cleavage site, was subjected to IMAC, a relatively weak binding was observed. About 87% of the total recovered activity was eluted in the presence of 35 mM imidazole, while the remaining activity was found in the 100 mM imidazole peak. These results with chimeric #3, further support the above conclusions that the strong binding of chimeric #1 to nickel immobilized to Chelating Sepharose is primarily due to the presence of the mbp (His-Asp-His-Asp-His-).

Example 6 Purification of mbp-HIV RT (Chimeric #2) from Crude *E. coli* Extract

The IMAC behavior of the following chimeric was studied.

2   Pro-Ile-His-Asp-His-Asp-His-Pro-Phe-His-Leu-Leu-Tyr-Tyr-Ser-RT

As shown in the elution profile of chimeric #2 from crude *E. coli* extract, about 70% of the total recovered activity was found in a sharp peak that was eluted at 100 mM imidazole. The weakly bound activity (25%) was eluted with 35 mM imidazole. Although not proven, this leakage of activity may be due to the truncation of the mbp in some molecules. As shown above, there is Tyr-Tyr sequence which is a good target site for chymotrypsin-like proteases. These tyrosines are not present in chimeric #1 which is likely to be less susceptible to proteolysis due to the absence of these tyrosines in the cleavage site. Other likely explanations are; partial exposure of mbp in some molecules and/or steric factors such that all the histidines are not utilized in the binding of some molecules to immobilized nickel.

Total protein recovery in the above experiment was 94%, the recovered RT activity was 96% of the total activity applied on the IMAC column. SDS-PAGE of various fractions obtained after IMAC of crude E. coli extract containing recombinant chimeric #2 shows that most of the E. coli contaminating proteins were eliminated in the 35 mM imidazole elution. As expected based on results on mbp-containing construct #1, mbp-containing HIV RT (chimeric #2) was purified away from the contaminating proteins. These studies further substantiate the role of alternating histidines in the purification of chimeric proteins containing the same.

Furthermore, a control chimeric (#4), Pro-Ile-Pro-Phe-His-Leu-Leu-Tyr-Tyr-Ser-RT, was also studied on a nickel IMAC column. The major RT activity peak obtained with this chimeric was eluted at 35 mM imidazole with no significant activity peak at a 100 mM imidazole concentration. SDS-PAGE showed that the chimeric #3 lacking the mbp was contaminated with E. coli proteins which co-eluted at 35 mM imidazole. It was concluded that strong and specific binding of chimeric #2 on a IMAC column is due to the presence of the mbp. These results also indicate that a change in the cleavage site has no significant effect on the mbp-based IMAC purification of HIV RT.

Example 7 Purification of mbp-β-Galactosidase from Crude E. coli Extract

After establishing that an mbp with 3 alternate histidines is a useful handle in the purification of HIV RT from crude E. coli extracts, we wanted to determine if its ability to bind to nickel could be transferred to another protein. Therefore, the IMAC of the following chimeric expressed in E. coli was investigated.

5 Pro-Ile-His-Asp-His-Asp-His-Pro-Phe-His-Leu-β-galactosidase

The elution profile of a crude E. coli extract containing the mbp-B-galactosidase chimeric shows three protein peaks. The first peak represents those E. coli proteins with no affinity for the metal ion which therefore appeared in the breakthrough volume. The middle peak was eluted in the presence of 35 mM imidazole. At 100 mM imidazole, another sharp protein peak was eluted. Factions 2, 20, and 38 from this elution profile were tested for the presence of the mbp by ELISA assay. In this study, two different bleedings from two different rabbits were used. Only fraction 38, representing the 100 mM imidazole peak was found to be reactive to polyclonals raised against a conjugated peptide containing the mbp. It was concluded that mbp-β-galactosidase was retarded completely on the IMAC column: The purity of the β-galactosidase was checked by SDS-PAGE. It is noteworthy here that only the β-galactosidase band appeared as the major band, indicating that a single-step purification of a chimeric with the mbp is feasible. When commercially available β-galactosidase, without the mbp, was allowed to pass through a nickel column, it bound to the column weakly as shown by its elution at 35 mM imidazole followed by SDS-PAGE. It was concluded from these studies that the alternate histidine sequence (His-Asp-His-Asp-His) is a useful handle for the affinity purification of chimeric proteins (HIV RT and β-galactosidase) via IMAC. Implications of these results in the IMAC purification of recombinant proteins are discussed below.

Example 8 Screening of Various Metals for Their Ability to Recognize the Metal Binding Peptide (mbp)

The metal binding peptide used in the present study is based on the use of alternating histidines as the primary contributing electron donor in the IMAC. We first compared the chromatographic behavior of chimeric #1 with HIV RT on various metal ions in an attempt to find the best metal ion for binding and elution purposes.

It was clear from experiments on the binding and elution of HIV RT to immobilized $Ni^{2+}$ and $Zn^{2+}$ that HIV RT binds very weakly to these metal ions and can be eluted by adding 10 mM imidazole. SDS-PAGE of samples obtained from this experiment indicate that most of the E. coli contaminating proteins are also eluted in the presence of 10 mM imidazole. This was a good indication that if strong binding to a metal ion via the linker can be achieved, it should be possible to achieve substantial purification in a single step. Therefore, the experiment was repeated using IMAC columns of $Cu^{2+}$, $Ni^{2+}$, and $Zn^{2+}$ and HIV RT with the metal binding peptide fused to its N-terminal (chimeric #1). Results show that chimeric #1 did not bind very strongly to copper, while binding to zinc and nickel was considered moderate and strong respectively. SDS-PAGE of samples obtained from nickel, zinc and copper columns during these experiments show that metal binding peptide (mbp)-containing RT (chimeric #1) was eluted at a much higher concentration of imidazole from nickel than copper and was very pure. It was concluded that nickel was the best metal ion for further IMAC studies on various mbp-containing chimeric proteins.

Example 9 Examples of Fusion Protein Constructions with Metal Chelating Peptide Interposed Between Two Polypeptides Examples of fusion proteins having a metal chelating peptide between two polypeptides can be represented by the formula:

Y-mbp-Z wherein Y and Z are desired polypeptides and mbp is a metal chelating peptide. In such cases, Y and Z can both be desired polypeptides. Alternatively, one of the two can be a polypeptide which drives gene expression. In either case Y, Z or both can have an adjacent cleavage site for post purification processing.

Specific constructions according to the formula Y-mbp-Z can be made by those having ordinary skill in the art using standard techniques.

Example 10 Fusion Proteins Comprising the Desired Protein and a Peptide Linker that is a Substrate for DPP I A strategy to purify DPP I-cleavable chimeric proteins from recombinant E. coli is described. It is based on a genetically engineered N-terminal extension with specificity both for a metal ion for purification and for DDP-I for cleavage of the same extension to generate the desired protein which contains Pro at position 2 and/or at position 3 as a stop signal. These are designed such that there are no prolines in the entire linker portion, no lysines or arginines at odd numbered positions in the linker and at least three alternating histidine residues. The stop signal for cleavage is provided by the 2nd and/or 3rd proline of the desired protein. Fusion proteins can comprise the above-described N-terminal extension linked to the HIV-1 trans-activator (Tat) protein as the desired protein portion. In such a fusion protein, DPP I cleavage can remove the metal chelating peptide (mop), thereby liberating the desired protein.

The preferred DPP I cleavable N-terminal extensions according to the present invention are outlined as follows:

Fusion protein containing HIV-1 trans-activator (Tat) and an N-terminal extension (mcp#1-Seq ID 1) linked to Tat (Tat/mcp#l):

Met-Glu-His-Glu-His-Glu-His-Glu-His-Glu-Tat

Fusion protein containing HIV-1 trans-activator Gat) and an N-terminal extension (mcp#2-Seq ID 2) linked to Tat (Tat/mcp#2):

Met-Glu-His-Asp-His-Asp-His-Asp-His-Asp-Tat

Fusion protein containing HIV-1 trans-activator (Tat) and an N-terminal extension (mcp#3-SEQ ID 3) linked to HIV-1 Tat (Tat/mcp#3):

Met-Ile-His-Asp-His-Asp-His-Asp-His-Asp-Tat

The N-terminal methionine is a consequence of protein biosynthesis in E. coli. It is not processed when Ile or Glu is the next amino acid.

Chimeric genes which encode these fusion proteins are constructed, inserted into and expressed in E. coli. Expressed proteins are purified using S-Sepharose chromatography and C-4 Reverse Phase HPLC. N-terminal sequencing is used to characterize the fusion proteins. Application of the alternating histidine-containing fusion proteins to the purification of recombinant proteins by IMAC and subsequent removal of the N-terminal extension by DPP I confirm the utility of the present invention.

Construction of Chimeric Genes Containing HIV-1 Tat Gene

All recombinant DNAs are prepared by standard techniques. Oligonucleotides corresponding to the metal chelating peptide/DPP I substrate sequence are constructed, purified, annealed and ligated to a gene encoding HIV-1 Tat (Tat) to form a chimeric gene. The Tat gene expression is described in Hasler, J. M., et al. (AIDS Research and Human Retroviruses: (1989) pp. 507–515). The chimeric gene is constructed using techniques well known to those having ordinary skill in the art.

To prepare expression vectors encoding a fusion protein comprising a linker that is a DPP I substrate and has alternating Histidines linked with the gene encoding Tat, a chimeric gene is constructed and inserted into an expression vector. Expression vectors containing the chimeric gene constructs are used to transform E. coli and expression of the genes in E. coli results in the production of the fusion proteins encoded by the chimeric genes. The molecular biology techniques used to produce and express the chimeric gene are well known to those having ordinary skill in the art. These fusion proteins contain the Tat amino acid sequence and an N-terminal extension that is a DPP I substrate which contains alternate histidines and is therefore a metal chelating peptide.

Preparation of Crude E. coli Extracts and Isolation of Fusion Proteins for Sequencing Approximately 3 g of E. coli cell paste from cells transformed with the desired expression vector is suspended in 30 ml of 0.25 M potassium phosphate, pH 7.2 containing 1 mM dithiothreitol (DTr), EDTA, phenylmethylsulfonyl fluoride (PMSF), and benzamidine HCL, 10 mg/liter aprotinin, leupeptin, and bestatin. This suspension is passed through a French Press three times to break the cells. Cell lysates are centrifuged at 12,000 rpm for 1 hr. The supernatant is removed and solid ammonium sulfate added to 40% saturation. After stirring for 1 hr, the suspension is centrifuged at 12,000 rpm for 1 hr. The supernatant is discarded and the pellet is redissolved in 2.25 mls of 50 mM Tris pH 7.5 containing 1 mM DTT, PMSF, and benzamidine. The solution is then dialyzed overnight into appropriate buffer for S-Sepharose ion-exchange chromatography followed by reverse phase HPLC. Purified Tat protein is used for characterization by N-terminal sequence analysis.

Purification of Fusion Proteins Using IMAC

The feasibility of using a metal chelating peptide for the purification of recombinant proteins from crude extracts can be demonstrated by using the following chimerics expressed in recombinant E. coli with HIV-1 Tat (Tat) as the model desired protein.

Fusion proteins Tat/mcp #1, Tat/mcp #2 and Tat/mcp #3 are each purified.

IMAC columns are prepared as follows. Chelating Sepharose Fast Flow from Pharmacia is washed thoroughly with Milli-Q water on a scintered glass filter. The gel is then resuspended in water to form a slurry. The slurry is poured carefully into a glass column (Pharmacia) to a volume of 6 mls (1×7 cm). After the gel has settled, the column is washed with 5 volumes of 50 mM EDTA (ethylenediaminetetraacetic acid) pH 8.0. Following this, the column is washed with 5 volumes of 0.2N NaOH and 5 volumes of Milli-Q water. The column then is charged with 5 volumes of 50 mM $NiSO_4$ (or $ZnCl_2$ or $CuSO_4$). Finally, the column is washed with 5 bed volumes of equilibration buffer. The equilibration buffer is made up of 20 mM Tris pH 8.0, containing 500 mM NaCl, 1 mM PMSF, 1 mM benzamidine, 10 mg/L leupeptin, and 10 mg/L aprotinin.

The column has been equilibrated with at least 5 volumes of equilibration buffer. 5–10 mls of crude recombinant E. coli extract are applied to the column by gravity. After all the crude material has entered the column, the column is washed with 10 column volumes of equilibration buffer containing 1.0M NaCl, instead of 500 mM NaCl, pH 8.0.

The column is then eluted with increasing concentrations of imidazole in the equilibration buffer at pH 8.0. For the earlier experiments, a large number of elutions are performed for each experiment to determine the concentration at which the chimeric is eluted. Later this elution is simplified and usually just three imidazole concentrations are used: 35 mM, 100 mM, and 300 mM imidazole in the equilibration buffer, pH 8.0. Ten bed volumes of each imidazole buffer are used. Between elutions, the column is washed with 10 volumes of equilibration buffer. Finally, the column is stripped with 5 bed volumes of 50 mM EDTA pH 8.0 to determine if any protein is still bound to the column. The flow rates for the columns are 1.0 ml/min. 5 ml fractions are collected. The columns are run at room temperature. Commercially available Pierce protein assay kits are used to determine the protein content of the samples.

Biological activity of purified Tat protein is determined by the method described incorporated herein by reference.

Conversion of the N-terminal extended fusion proteins to mature proteins

Commercially available DPP I from beef spleen (Boehfinger Mannheim, Indianapolis, Ind.) with a specific activity of 3000 U/mg protein is used. Enzymatic conversion is carried out by incubating the chimeric protein in 20 mM tris/500 mM NaCl, pH 8, at a enzyme to substrate ratio of 1:100 (w/w) for 60 rain at 25° C. The desired polypeptide is recovered from the uncleaved chimeric protein by IMAC followed by gel filtration. The authenticity is confirmed by N-terminal sequence analysis.

I claim:

1. A fusion protein represented by the formula
$R_1$-(His-X)$_n$-$R_2$
wherein (His-X)$_n$ represents a metal-chelating peptide;
n=3 to 6
each X is selected from the group consisting of Asp, Pro, Glu, Ala, Gly, Val, Ser, Leu, Ile and Thr; and
$R_2$ is a desired polypeptide directly or indirectly covalently linked to the metal-chelating peptide, and $R_1$ is a hydrogen or one or more amino-acid residues.

2. A fusion protein according to claim 1, wherein each X is independently selected from the group consisting of Asp, Glu and Pro.

3. A fusion protein according to claim 2, wherein each X is independently selected from the group consisting of Asp and Pro.

4. A fusion protein according to claim 1, wherein $R_2$ comprises a protein selected from the group consisting of tPA, IL-1, bSt, IL-1 inhibitor, CD4, HIV RT, human nerve growth factor, sCD4-PE40, human respiratory syncytial virus (RSV) FG chimeric glycoprotein, and PE40.

5. A fusion protein according to claim 4, wherein $R_2$ is a desired polypeptide indirectly covalently linked to the metal-chelating peptide, a cleavage site being interposed between the desired polypeptide and the metal-chelating peptide.

6. A fusion protein according to claim 5, wherein the cleavage site is an endopeptidase site cleavable by human renin.

7. A fusion protein according to claim 6, wherein $R_1$-(His-X)$_n$-$R_2$ includes a DPP I substrate.

8. A fusion protein according to claim 8, wherein Pro is the 2nd and/or 3rd amino-acid residue of the desired polypeptide of the fusion protein.

9. A method of purifying a fusion protein according to claim 1, comprising the steps of (a) contacting immobilized metal ions, said metal ions selected from the group consisting of nickel, zinc and copper ions, with cell extract material which contains cellular proteinaceous molecules including the fusion protein, wherein the fusion protein forms an affinity bond to the metal ions;

(b) removing cell extract material not bonded to the metal ions;

(c) eliminating the affinity bond; and (d) collecting purified fusion protein.

10. A method of purifying a fusion protein according to claim 1, wherein $R_2$ is a desired polypeptide indirectly covalently linked to the metal-chelating peptide, a cleavage site being interposed between the desired polypeptide and the metal-chelating peptide, comprising the steps of:

(a) contacting immobilized metal ions with cell extract material which contains cellular proteinaceous molecules including the fusion protein, where the fusion protein forms an affinity bond to the metal ions;

(b) removing cell extract material not bonded to the metal ions;

(c) eliminating the affinity bond;

(d) collecting purified fusion protein; and (e) cleaving the fusion protein at the cleavage site, to give the desired polypeptide and the metal-chelating peptide.

11. A method according to claim 9, which comprises the further step of removing the metal-chelating peptide from the fusion protein by DPP I cleavage.

12. A kit for purifying a fusion protein according to claim 1 comprising:

(a) a DNA molecule which encodes the metal-chelating peptide fused with a DNA molecule which encodes a desired polypeptide to form a chimeric gene encoding the fusion protein; and (b) a column containing immobilized metal ions.

13. A kit according to claim 12, wherein the DNA molecule further encodes a cleavage site.

14. A kit according to claim 13, wherein the cleavage site is an endopeptidase site cleavable by human renin.

15. A kit according to claim 14, wherein the metal-chelating peptide is a dipeptidylpeptidase I substrate.

* * * * *